United States Patent
Standke et al.

(10) Patent No.: US 10,259,832 B2
(45) Date of Patent: Apr. 16, 2019

(54) METHOD FOR PRODUCING AQUEOUS HYDROLYSATES FROM AMINOALKYLTRIALKOXYSILANES

(71) Applicant: Evonik Degussa GmbH, Essen (DE)

(72) Inventors: Burkhard Standke, Loerrach (DE); Christian Wassmer, Hausen (DE); Irene Lippert, Rheinfelden (DE); Kerstin Bibbo, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/576,289

(22) PCT Filed: Apr. 1, 2016

(86) PCT No.: PCT/EP2016/057183
§ 371 (c)(1),
(2) Date: Nov. 22, 2017

(87) PCT Pub. No.: WO2016/188654
PCT Pub. Date: Dec. 1, 2016

(65) Prior Publication Data
US 2018/0127442 A1    May 10, 2018

(30) Foreign Application Priority Data
May 28, 2015   (EP) ................................ 15169684

(51) Int. Cl.
| | |
|---|---|
| *C07F 7/18* | (2006.01) |
| *C08G 77/00* | (2006.01) |
| *B01D 3/42* | (2006.01) |
| *B01J 19/00* | (2006.01) |
| *C07B 41/02* | (2006.01) |
| *C07C 29/09* | (2006.01) |
| *C07C 31/04* | (2006.01) |
| *C07C 31/08* | (2006.01) |
| *C03C 25/66* | (2006.01) |
| *C08G 77/26* | (2006.01) |

(52) U.S. Cl.
CPC .............. *C07F 7/1804* (2013.01); *B01D 3/42* (2013.01); *B01J 19/0013* (2013.01); *C03C 25/66* (2013.01); *C07B 41/02* (2013.01); *C07C 29/09* (2013.01); *C07C 31/04* (2013.01); *C07C 31/08* (2013.01); *C07F 7/1892* (2013.01); *C08G 77/00* (2013.01); *C08G 77/26* (2013.01)

(58) Field of Classification Search
None
See application file for complete search history.

(56) References Cited

U.S. PATENT DOCUMENTS

| 5,679,147 | A | 10/1997 | Standke et al. |
| 6,512,132 | B2 | 1/2003 | Isoda et al. |
| 6,534,667 | B1 * | 3/2003 | Standke ............... C08K 5/544 |
| | | | 106/287.11 |
| 2003/0004365 | A1 | 1/2003 | Isoda et al. |

FOREIGN PATENT DOCUMENTS

EP    1 031 593 A2    8/2000

OTHER PUBLICATIONS

International Search Report and Written Opinion dated Jul. 8, 2016 in PCT/EP2016/057183 filed Apr. 1, 2016.
European Search Report dated Nov. 26, 2015, in European Patent Application No. 15169684.6 filed May 28, 2015.

* cited by examiner

*Primary Examiner* — Clinton A Brooks
*Assistant Examiner* — Kofi Adzamli
(74) *Attorney, Agent, or Firm* — Grüneberg and Myers PLLC

(57) ABSTRACT

The present invention relates to a process for preparing aqueous hydrolysates of aminoalkyltrialkoxysilanes by
(a) initially charging water, optionally heating,
(b) adding hydrolysable silanes consisting of at least one aminoalkyltrialkoxysilane in an amount which provides a molar ratio of water to total amount of aminoalkyltrialkoxysilane of 10.5 to 20, and
(c) distilling off the alkyl alcohol formed in the reaction, wherein the solids content in an aqueous composition thus prepared is 30% to 55% by weight, based on the composition, and the aqueous solution has a total content of free and bound alkyl alcohol of not more than 1% by weight, based on the composition.

13 Claims, No Drawings

METHOD FOR PRODUCING AQUEOUS HYDROLYSATES FROM AMINOALKYLTRIALKOXYSILANES

The present invention relates to a process for preparing aqueous hydrolysates of aminoalkyltrialkoxysilanes which leads to concentrated aqueous solutions of these aminoalkyltrialkoxysilanes that are essentially free of alcohols, and is performable in a particularly economically viable manner.

The prior art discloses processes in which aminoalkyltrialkoxysilanes, for example 3-aminopropyltriethoxysilanes, are co-hydrolysed with additional hydrolysable silanes, for example bis(triethoxysilyl)propylamine and/or alkyltrialkoxysilanes and/or functionally substituted alkyltrialkoxysilanes, where the functional group differs from the amino group. Such processes are known, for example, from EP-A 675 128, EP-A 716 127, EP-A 997 469, EP-A 1 031 593 and WO 2009/03538. By contrast, the present invention relates to a process for preparing hydrolysates of aminoalkyltrialkoxysilanes having a relatively high solids content and in which no further hydrolysable silanes other than aminoalkyltrialkoxysilanes are present.

DE 103 33 941 A1 relates to a size composition for glass fibres which comprises, as well as water, a film former and an adhesion promoter. An adhesion promoter suggested is a hydrolysate of 3-aminopropyltriethoxysilane. In the sole working example, without giving further details as to the process regime, γ-aminopropyltriethoxysilane is hydrolysed with a more than 400-fold molar excess of water.

EP-A 1 017 880 discloses a process for coating a metal substrate, in which a treatment solution is applied to the surface of the metal substrate, wherein the treatment solution contains a partially hydrolysed aminosilane and a fluorine-containing inorganic acid in a ratio of 1:2 to 2:1. The partially hydrolysed aminosilane is hydrolysed by adding very small amounts of water in the range from 4% to 5%, based on the total volume of water and aminosilane, by leaving it to stand overnight.

U.S. Pat. No. 3,810,843 relates to the preparation of compositions by contacting a silica sol with an organofunctional silane coupling agent that has been hydrolysed in an aqueous system beforehand. Among the coupling agents proposed is 3-aminopropyltriethoxysilane. The general description of the publication does not contain any details as to the process by which the hydrolysate of the silane coupling agent is prepared. In a specific embodiment, 3-aminopropyltriethoxysilane is added to a dilute aqueous sodium hydroxide solution, where the molar ratio of water to 3-aminopropyltriethoxysilane is 26.7%.

Zengping Zhang et al. describe, in "Journal of Applied Polymer Science", 103, 2608-2614 (2007), the preparation of octa(aminopropylsilsesquioxanes) having a cage structure. In this case, for example, 3-aminopropyltriethoxysilane is hydrolysed in a mixture of acetonitrile and 1-propanol in the presence of tetraethylammonium hydroxide, where the molar ratio of water to silane is 8.9:1, in order to prepare the desired cage structures.

U.S. Pat. No. 6,512,132 likewise relates to a process for preparing aqueous hydrolysates of 3-aminopropyltriethoxysilane. The objective is likewise the provision of those hydrolysates that are essentially free of organic solvents, especially alcohol, and have a high storage stability. The storage stability is determined by measuring the colour number after storage over a defined period. According to the general teaching of publication, the aqueous solution is prepared by reacting 1 mol of aminoalkylsilane with 1.5-10 mol of water and distilling off the volatile organic compound which is formed through the hydrolysis reaction. In the specific working example, water is added to an initial charge of 3-aminopropyltriethoxysilane. According to the general teaching, the hydrolysis is conducted within a temperature range from 0° C. to 150° C. The specific embodiments do not contain any teaching about the hydrolysis temperature. By contrast with the general teaching, in example 2, the 3-aminopropyltriethoxysilane is hydrolysed with water in a molar ratio of water to silane of 12.4. According to the teaching of U.S. Pat. No. 6,512,132, aqueous hydrolysates of 3-aminoalkyltriethoxysilane are obtained in high concentrations in the order of magnitude of 50% by weight, and are also substantially free of alcohol formed through hydrolysis. However, the process described leads to a comparatively low space-time yield. Thus, it is a great disadvantage of the procedure according to U.S. Pat. No. 6,512,132 that such a mode of preparation of said products requires a long metering or stirring time for the required amount of water and, in addition, there is regular occurrence of significant flocculations or separations associated with a considerable rise in viscosity during the preparation process, which results in more prolonged and intensive expenditure of stirring energy, in order to achieve adequate product homogeneity. Furthermore, such separations can in practice disrupt production operation to a crucial degree as a result of deposits or blockages, associated with necessary shutdown times for cleaning measures.

Likewise commercially available are aqueous hydrolysates of 3-aminopropylsilanes, for example Dynasylan® HYDROSIL 1151. These aqueous solutions are likewise substantially free of organic solvents. However, the solids content of these solutions is comparatively low and is in the region of 20% by weight. Various disadvantages are associated with this low concentration of hydrolysed silane in the commercial products. These are especially elevated transport costs, since a large amount of water and a small amount of active ingredient is transported. Furthermore, the dilute solutions freeze at temperatures not far below zero, such that high transport costs arise as a result of the need for heated transport in the case of low outside temperatures. The dilute products contain a large amount of water and thus cannot be employed where high amounts of water are disadvantageous. Furthermore, it is not possible to formulate concentrates with dilute solutions.

It is therefore an object of the present invention to provide a specific process of maximum economic viability which, under comparable apparatus conditions with at least comparatively high or better space-time yields, leads to more highly concentrated hydrolysates of aminoalkyltrialkoxysilanes, i.e. a higher solids content, and a composition thus obtained is simultaneously essentially free of organic solvents, i.e. especially has a minimum level of VOCs (volatile organic compounds).

Hereinafter, said aminoalkyltrialkoxysilanes are also called hydrolysable silanes or silanes for short.

This object was surprisingly achieved by a specific process for preparing aqueous hydrolysates of aminoalkyltrialkoxysilanes by
(a) initially charging water, optionally heating,
(b) adding hydrolysable silanes consisting of at least one aminoalkyltrialkoxysilane in an amount which provides a molar ratio of water to total amount of aminoalkyltrialkoxysilane of 10.5 to 20:1, and
(c) distilling off the alkyl alcohol formed in the reaction, wherein a solids content in an aqueous solution thus obtainable (also referred to hereinafter as aqueous composition or composition for short) of 30% to 55% by weight, based on the composition, is advantageously achieved, with simultaneously a comparatively high space-time yield under comparable experimental conditions in terms of apparatus and with an extremely low VOC content. Thus, particularly because of the present mode of operation, shorter metering times and shorter and less intensive stirring periods were enabled and hence, not least in an energy-saving manner, a distinct improvement in economic viability was achieved. Furthermore, in the case of the mode of operation of the invention, there is also no longer any occurrence of precipitations during the preparation process, as a result of which it was possible to lower the risk of deposits or blockages in the production plant and distinctly reduce shutdown times.

The invention therefore provides a process for preparing aqueous hydrolysates of aminoalkyltrialkoxysilanes by
(a) initially charging water, optionally heating,
(b) adding hydrolysable silanes consisting of at least one aminoalkyltrialkoxysilane in an amount which provides a molar ratio of water to total amount of aminoalkyltrialkoxysilane of 10.5 to 20:1, and
(c) distilling off the alkyl alcohol formed in the reaction, wherein the solids content in an aqueous composition thus prepared is 30% to 55% by weight, based on the composition, and the aqueous solution has a total content of free and bound alkyl alcohol of not more than 1% by weight, based on the composition.

Aminoalkyltrialkoxysilanes suitable for the use according to the present invention may be selected from compounds of the general formula

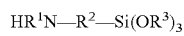

in which
R$^1$ is selected from H or a C$_1$-C$_4$-alkyl group;
R$^2$ is selected from a bivalent C$_1$-C$_4$-alkyl group; and
R$^3$ is selected from a C$_1$-C$_3$-alkyl group.
R$^1$ is preferably hydrogen. R$^2$ is preferably a bivalent propyl group [—(CH$_2$)$_3$—]. R$^3$ is preferably selected from methyl and ethyl.

Particularly preferred aminoalkyltrialkoxysilanes are 3-aminopropyltriethoxysilane or 3-aminopropyltrimethoxysilane or mixtures thereof, 3-aminopropyltriethoxysilane being the most preferred.

In the process according to the invention for preparing aqueous hydrolysates of aminoalkyltrialkoxysilanes, the water required for hydrolysis is initially charged and the hydrolysable silanes consisting of at least one aminoalkyltrialkoxysilane are added. It is essential to the invention in this context that the amounts of aminoalkyltrialkoxysilane and water are chosen such that, on completion of addition of the aminoalkyltrialkoxysilanes to the initial charge of water, a molar ratio of water to the total amount of aminoalkyltrialkoxysilane of 10.5 to 20:1, especially of 11 to 18:1, including 12:1, 13:1, 14:1, 15:1, 16:1, 17:1, is provided.

The objective of the present invention is to provide an aqueous solution of aminoalkyltrialkoxysilanes which is essentially free of organic solvent, especially of the alcohol released in the hydrolysis, and which releases essentially no organic solvents, especially the alcohol formed as a result of the hydrolysis, even after any dilution with water. "Essentially free" in the context of the present invention means that the aqueous solution obtained has a content of organic solvents, especially a total content of free alkyl alcohol and bound alkyl alcohol that could be released by hydrolysis, of not more than 1% by weight, based on the composition, preferably of not more than 0.7% by weight down to the detection limit, measured after hydrolysis of a sample of the aqueous solutions with sulphuric acid and subsequent neutralization with aqueous sodium carbonate solution by means of gas chromatography (for the exact method for measurement of the total content of alkyl alcohol see examples).

It has been found that, surprisingly, in the process according to the invention, the starting aminoalkyltrialkoxysilane is essentially fully hydrolysed after only comparatively short addition/metering or stirring times in step (b) of the process, and no precipitations occur. More particularly, after the addition of the aminoalkyltrialkoxysilane has ended, no further reaction time is required to attain the above-specified values for total alkyl alcohol, and it is possible immediately after the addition has ended to commence the distillative removal of the alkyl alcohol formed in the reaction (step (c)). As a result, by comparison with the prior art, under comparable apparatus conditions, a distinct improvement in space-time yields (STY) can be achieved in the process according to the invention, as a result of which it is possible to distinctly improve the economic viability of a process for preparing aqueous hydrolysates of aminoalkyltrialkoxysilanes without any resultant deterioration in the product properties of the aqueous solutions obtained.

Thus, the period of time between the end of the addition of the aminoalkyltrialkoxysilanes and commencement of the distillative removal of the alkyl alcohol may be less than 5 minutes after attainment of the preferred or required distillation conditions, i.e. after establishment of pressure and temperature in the reaction/distillation unit, preferably less than 3 minutes, more preferably less than 1 minute, especially with no further production delay [abbreviations also used hereinafter: min=minute(s) and h=hour(s)].

Preferably, the internal reactor temperature on commencement of the addition of the aminoalkyltrialkoxysilanes in step (b) is 25° C. to 50° C., more preferably 30° C. to 45° C. Since the hydrolysis reaction of aminoalkyltrialkoxysilane is exothermic, the reaction mixture is heated on addition of the aminoalkyltrialkoxysilanes to the initial charge of water. Therefore, it has been found to be advantageous to adjust the duration of addition in step (b) such that the internal reactor temperature at the end of the addition of the aminoalkyltrialkoxysilanes in step (b) is 50° C. to 80° C., preferably 55° C. to 70° C., more preferably 55° C. to 65° C. The duration of the addition of the aminoalkyltrialkoxysilane in step (b) is therefore preferably 20 to 240 min, more preferably 30 to 120 min, especially preferably 35 to 90 min and most preferably 40 to 60 min.

After the hydrolysis reaction has ended, in step (c) of the process according to the invention, the alkyl alcohol formed in the reaction is distilled off. After the alkyl alcohol formed has been distilled off, the content of free alkyl alcohol should be not more than 1% by weight, preferably not more than 0.7% by weight, measured by means of gas chromatography (for the exact method for measurement of the free alcohol see the examples). Preferably, the alcohol formed through the hydrolysis is distilled off under reduced pressure. A suitable pressure range for the vacuum distillation is 80 to 400 mbar, preferably 100 to 350 mbar, at a temperature of 30° C. to 70° C., preferably 35° C. to 60° C. To establish the desired concentration of the aqueous solution obtained as reaction product or to adjust the viscosity of the aqueous solution, the amount of alkyl alcohol distilled off, or mixture of water and alkyl alcohol, can be at least partly replaced by water.

The process according to the invention affords an aqueous solution of a hydrolysate of hydrolysable silanes, consisting of at least one aminoalkyltrialkoxysilane having a high solids content in the range from 45% to 55% by weight, measured according to DIN 38409-H1-1.

The aqueous solutions of the invention are visually clear, essentially colourless, aqueous solutions. More particularly, it has been found that, surprisingly, the solutions according to the invention are colourless even after prolonged storage.

Thus, the solutions according to the invention are especially suitable for applications where it is undesirable when the colour of the system is altered by aqueous solutions of hydrolysates of aminoalkyltrialkoxysilane. This relates particularly to the use of the aqueous solution of the invention in resin or varnish systems, especially colourless resin and varnish systems.

In addition, the solutions according to the invention are visually clear and preferably have a turbidity value of 5 FNU or less, more preferably 3 FNU or less, especially 2 FNU or less and most preferably 1 FNU or less, measured according to ISO 7027.

The aqueous solutions according to the invention are advantageously obtained in the process according to the invention with a solids content of 30% to 55% by weight, based on the composition, preferably of 40% to 55% by weight, more preferably of 44% to 54% by weight, especially 50% to 53% by weight.

Because of the high solids concentration, the aqueous solutions according to the invention have numerous advantages over the known commercial products. Thus, the aqueous solutions have a freezing point in the range from −7° C. to −18° C., preferably from −9° C. to −17° C., more preferably between −10° C. and −16° C., at a pressure of 1 atm. This means that the solutions according to the invention are much more frost-resistant and need not be transported in heated transport in the case of correspondingly low temperatures, as a result of which it is possible to reduce the energy costs once again.

Furthermore, the high solids content results in a distinct reduction in the transport costs based on the mass of aminoalkyltrialkoxysilane hydrolysate. Furthermore, the aqueous solutions according to the invention are particularly suitable for production of concentrates, since much less water is introduced compared to the commercially available products.

In general, the process according to the invention can be conducted as follows:

A suitable apparatus, for example consisting of a reactor with metering and withdrawal devices, heating/cooling device including measurement and control unit, and reflux condenser, mixing unit, distillation unit including pressure-reducing device, is initially charged with the water and optionally heated to the desired temperature, preferably to a temperature of 25 to 50° C., especially to a temperature in the range from 30 to 45° C., and, while mixing, the aminoalkyltrialkoxysilane is metered in in an amount corresponding to the molar ratio of water to the total amount of aminoalkyltrialkoxysilane of 10.5 to 20:1. A suitable mode of operation is under protective gas, for example under nitrogen. Subsequently, the alkyl alcohol formed in the reaction is distilled off and the process product is obtained.

Aqueous solutions obtained in accordance with the invention—optionally also after dilution, for example with demineralized water—advantageously find use for the coating of glass fibres or rockwool, for the silanization of fillers, as adhesion promoter, especially for the improvement of the adhesion of organic polymers to inorganic surfaces, for production of anticorrosion concentrates, for modification of resin systems, especially aminoplast-formaldehyde resins or phenolic resins, for the improvement of rheological properties, especially of aqueous polymer dispersions and emulsions, as crosslinker, as modifier for paints and varnishes.

The present invention is elucidated in detail hereinafter with reference to the appended working examples, without restricting the subject-matter of the invention thereto:

EXAMPLES

The test methods for characterization of the properties of the aqueous solutions which are prepared by the process according to the invention, as specified in the description, the examples and the claims, were conducted as follows:

| | |
|---|---|
| Solids [% by weight] | The solids content was determined according to DIN 38409-H1-1. |
| $SiO_2$ [% by weight] | The $SiO_2$ determination was conducted according to the following description: 1 g of a sample was weighed into a 250 ml beaker. One Kjeldahl tablet (Merck No. 15348) and 20 ml of concentrated sulphuric acid were added. The solution was heated gradually until $SO_3$ vapours formed. After cooling, the solution was cautiously diluted to 200 ml with distilled water. The precipitated silica was filtered through a white-band filter paper. The filter residue was washed with distilled water until the filtrate became neutral (pH > 4). The filter paper was dried and converted to ash in a platinum crucible. The residue was burnt at 800° C. and weighed. After treatment with concentrated hydrofluoric acid, the residue was burnt again at 800° C. and weighed.<br>$SiO_2$ [% by weight] = 100 m/E<br>m = difference in weight before and after the treatment with hydrofluoric acid in g<br>E = weight of the sample in g. |
| Viscosity (20° C.) [mPas] | Determination according to DIN 53015 |
| Density (20° C.) [g/ml] | Determination according to DIN 51757 |
| Refractive index (20° C.) | DIN 51423 determination |
| Turbidity [FNU] | Determination according to ISO 7027 |
| Total alcohol (alcohol, after hydrolysis) [% by weight] | The total alcohol determination was conducted according to the following description: 5 g of a sample were weighed into a flask and hydrolysed with 25 ml of sulphuric acid (20%). After addition of 75 ml of distilled water, the solution was neutralized with sodium carbonate solution (20%) and then subjected to a steam distillation. The distillate was collected in a 250 ml flask. According to the expected alcohol content, up to 3 ml of sec-butanol were added and the flask was made up to the mark with |

| | distilled water. The alcohols were analysed quantitatively by means of gas chromatography using a capillary column with an FID and appropriate data processing (HP 7820 with OpenLab). Solutions of the expected alcohols and sec-butanol were used for calibration purposes. The sec-butanol served as internal standard. The total alcohol content thus determined in the sample includes the proportion of free alcohol and alcohol bound in the form of hydrolysable alkoxy groups. |
|---|---|
| Free alcohol (ethanol) [% by weight] | The determination of the content of free alcohol was conducted according to the following description: 2 g of a sample and 50 mg of 2-butanol as internal standard are dissolved in 10 g of demineralized water. This solution is analysed quantitatively by means of capillary column with a TCD and appropriate data processing (HP 7820 with OpenLab). The calibration is effected with a solution of 50 mg of the relevant alcohol and 50 mg of the internal standard used in 10 g of the solvent used. |

The space-time yield (STY) reported in the examples was calculated as follows:

$$STY = \frac{\text{Yield calculated as silicon } (Si) \text{ in } [g]^{1)}}{\sum (\text{volume of reactants}) \; [l]^{2)} \times \text{preparation time } [h]^{3)}}$$

[1] Yield $(Si)$ = yield $[g] \times w(Si)$ in $\% \times 0.01$

"$(Si)$" or "$w(Si)$" was calculated here on the basis of the respective $SiO_2$ determination

[2] Reactants refer to the amounts of water and 3-*aminopropyltriethoxysilane* (*AMEO*) initially charged and the amounts of *AMEO* and water metered in. The density for the reactants used was assumed simply to be 1.0 g/cm³. This is used to calculate the volume of reactants from the quotient of $\Sigma(m_{reactants})$ and the density of 1.0 g/cm³.

[3] Preparation time = time from the start of the reaction (dropwise addition of *AMEO* or water) to the end of the distillation Example 1

A 2 l four-neck flask with precision glass stirrer, dropping funnel, distillation apparatus, jacketed coil condenser, rotary vane oil pump, bottom thermometer, top thermometer and oil bath with temperature regulation was initially charged with 800.0 g (44.4 mol) of demineralized water under an $N_2$ blanket, and heated to a bottom temperature of 40.7° C. with the oil bath. After the oil bath had been removed, without further heating, 800.0 g (3.61 mol) of Dynasylan® AMEO were added dropwise within 44 min. In the course of this, the bottom temperature rose to 57.5° C. There was minimal turbidity for about 6 min, then the bottoms liquid was colourless and clear. After the dropwise addition has ended, reduced pressure was applied immediately. At a reduced pressure of 304 to 122 mbar, bath temperature 105° C. to 115° C., a bottom temperature of 46.3° C. to 50.7° C., top temperature of 44.4° C. to 49.4° C., 842.7 g of ethanol/water were distilled off within 2.3 h (hydrolysis alcohol+73%). After about 500 g had been distilled off, dropwise addition of 579.2 g of demineralized water was commenced and lasted until the end of the distillation. During the reaction and distillation, there was no precipitation or significant rise in viscosity. After the distillation had ended, the reactor was vented with nitrogen.

The yield was 1320.22 g of clear colourless product.

| | |
|---|---|
| The space-time yield was | 21.3 [g (Si)/(l × h)]. |
| Solids content | 30.7% by weight |
| Total alcohol | 0.7% by weight |

The analysis data of the product obtained are compared once again in summary in Table 1.

Comparative Example 1 (Cf. Example 2 from U.S. Pat. No. 6,512,132)

A 2 l four-neck flask with precision glass stirrer, dropping funnel, distillation apparatus, jacketed coil condenser, rotary vane oil pump, bottom thermometer, top thermometer and oil bath with temperature regulation was initially charged with 800.0 g (3.61 mol) of Dynasylan® AMEO under an $N_2$ blanket, and heated to a bottom temperature of 41.4° C. with the oil bath. After the oil bath had been removed, without further heating, 800.0 g (44.4 mol) of demineralized water were added dropwise within 2 h. In the course of this, the bottom temperature rose to 65.4° C. and significant exothermicity was apparent. Significant precipitation arose over a period of about 8 min, with white flakes, some of which were large. Subsequently, the bottoms liquid was colourless and clear. After the dropwise addition has ended, reduced pressure was applied immediately. At a reduced pressure of 204 to 198 mbar, bath temperature 109° C. to 111° C., a bottom temperature of 46.8° C. to 59.9° C., top temperature of 42.8° C. to 51.3° C., 701.6 g of ethanol/water were distilled off within 2 h (hydrolysis alcohol+40%). After cooling to about 38° C., the reactor was vented with nitrogen and the product was diluted with 435.6 g of demineralized water within about 15 min and hence adjusted to an active content of 60%.

The yield was 1324.4 g of clear colourless product.

| | |
|---|---|
| The space-time yield was | 11.2 [g (Si)/(l × h)]. |
| Solids content | 30.8% by weight |
| Total alcohol | 1.4% by weight |

The analysis data of the product obtained are compared once again in summary in Table 1.

Example 2

A 2 l four-neck flask with precision glass stirrer, dropping funnel, distillation apparatus, jacketed coil condenser, rotary vane oil pump, bottom thermometer, top thermometer and oil bath with temperature regulation was initially charged with 800.0 g (44.4 mol) of demineralized water under an $N_2$ blanket, and heated to a bottom temperature of 40.2° C. with the oil bath. After the oil bath had been removed, without further heating, 800.0 g (3.61 mol) of Dynasylan® AMEO were added dropwise within 40 min. In the course of this, the bottom temperature rose to 58.2° C. Minimal turbidity arose, which disappeared after the end of dropwise addition; the bottoms liquid was colourless and clear. Thereafter, reduced pressure was applied immediately. At a reduced pressure of 326 to 101 mbar, bath temperature 108° C. to 110° C., a bottom temperature of 48.4° C. to 52.9° C., top temperature of 46.7° C. to 49.6° C., 872.0 g of ethanol/water were distilled off within 2.4 h (hydrolysis alcohol+73%). After about 700 g had been distilled off, 46.9 g of demineralized water were added dropwise for dilution within 10 min. Toward the end of the distillation, the bottoms liquid was viscous but still efficiently stirrable. After cooling, the system was vented with nitrogen.

The yield was 762.9 g of clear colourless product.

| | |
|---|---|
| The space-time yield was | 21.1 [g (Si)/(l × h)]. |
| Solids content | 52.8% by weight |
| Total alcohol | 0.2% by weight |

The analysis data of the product obtained are compared once again in summary in Table 1.

Comparative Example 2: (Cf. Example 1 from U.S. Pat. No. 6,512,132)

A 2 l four-neck flask with precision glass stirrer, dropping funnel, distillation apparatus, jacketed coil condenser, rotary vane oil pump, bottom thermometer, top thermometer and oil bath with temperature regulation was initially charged with 1000.0 g (4.52 mol) of Dynasylan® AMEO under an $N_2$ blanket, and heated to a bottom temperature of 40.1° C. with the oil bath. After the oil bath had been removed, without further heating, 500.0 g (27.8 mol) of demineralized water were added dropwise within 1.25 h. In the course of this, the bottom temperature rose to 65.5° C. and significant exothermicity was apparent. Significant precipitation arose over a period of about 18 min, with white flakes, some of which were large. After the dropwise addition had ended, reduced pressure was applied immediately. At a reduced pressure of 216 to 205 mbar, bath temperature 108° C. to 113° C., a bottom temperature of 46.9° C. to 52.9° C., top temperature of 42.6° C. to 48.3° C., 703.4 g of ethanol/water were distilled off within 1.65 h (hydrolysis alcohol+20%). During the distillation, there was a very significant rise in viscosity. At this point, the bottoms were no longer stirrable. The bottoms were solid (active content 125.5%). The system was vented immediately with nitrogen, and 250.4 g of demineralized water were added to the bottoms. In order to get the solids back into solution, the flask was agitated on an RO 10 agitator for 5.25 h. Thereafter, the bottoms were almost completely back in solution. Only on the stirrer paddle was a little solid still present.

The yield was 1037.6 g of clear colourless product.

| | |
|---|---|
| The space-time yield is | 11.7 g Si/(l × h). |
| The space-time yield was | 11.7 [g (Si)/(l × h)]. |
| Solids content | 48.6% by weight |
| Total alcohol | 6.5% by weight |

The analysis data of the product obtained are compared once again in summary in Table 1.

Example 3

An 8 l four-neck jacketed flask with precision glass stirrer, dropping funnel, distillation apparatus, column with 4 Sulzer EX packing elements L=5 cm, W=4 cm (theoretical plates at moderate load 13-20), jacketed coil condenser, rotary vane oil pump, bottom thermometer, top thermometer, thermostat and Prominent Gamma 4 metering pump was initially charged with 3401.8 g (188.8 mol) of demineralized water under an $N_2$ blanket, and heated to a bottom temperature of 40.0° C. with the thermostat. At this bottom temperature (bath temp. 60° C.), 3400.1 g (15.4 mol) of Dynasylan® AMEO were metered in by means of a metering pump within 1 h. In the course of this, the bottom temperature rose to 63.9° C. The bottoms liquid remained colourless and clear. Thereafter, reduced pressure was applied immediately. At a reduced pressure of 106 to 105 mbar, thermostat temperature 96.8° C. to 105° C., a bottom temperature of 37.8° C. to 47.7° C., top temperature of 36.6° C. to 46.9° C., 3719.3 g of ethanol/water were distilled off within 4.75 h (hydrolysis alcohol+75%). After about 1348.71 g had been distilled off, a total of 782.9 g of demineralized water were added dropwise during the distillation for dilution within 2.5 h. The bottoms liquid was colourless, clear and nonviscous during and toward the end of the distillation. There were no precipitates and deposits whatsoever at the edge of the flask. After cooling, the system was vented with nitrogen.

The yield was 3897.2 g of clear colourless product.

| | |
|---|---|
| The space-time yield was | 12.0 [g(Si)/(l × h)]. |
| Solids content | 44.7% by weight |
| Total alcohol | 0.3% by weight |

The analysis data of the product obtained are compared once again in summary in Table 1.

Comparative Example 3

An 8 l four-neck jacketed flask with precision glass stirrer, dropping funnel, distillation apparatus, column with 4 Sulzer EX packing elements L=5 cm, W=4 cm (theoretical plates at moderate load 13-20), jacketed coil condenser, rotary vane oil pump, bottom thermometer, top thermometer, thermostat and Prominent Gamma 4 metering pump was initially charged with 3406.5 g (15.4 mol) of Dynasylan® AMEO under an $N_2$ blanket, and heated to a bottom temperature of 39.9° C. with the thermostat. At this bottom temperature (bath temp. 60° C.), 3400.5 g (188.8 mol) of demineralized water were metered in by means of a metering pump within 2.75 h. In the course of this, the bottom temperature rose to 72.7° C. Very significant exothermicity was apparent. After about 225 ml of demineralized water had been metered in, white flakes and deposits formed at the edge of the flask. The bottoms liquid was milky white. After a further 7 min (300 ml of demineralized water in total), the flakes and turbidity were back in solution; the bottoms liquid remained colourless and clear. After all the demineralized water had been metered in, reduced pressure was applied immediately. At a reduced pressure of 107 to 100 mbar, thermostat temperature 81° C. to 105° C., a bottom temperature of 37.8° C. to 47.7° C., top temperature of 35.2° C. to 50.9° C., 3820.3 g of ethanol/water were distilled off within 5.6 h (receiver+cold trap) (hydrolysis alcohol+80%). After about 1632.4 g had been distilled off, gel-like deposits occurred at the edge of the flask, which accumulated further during the distillation. The bottoms liquid was viscous, colourless and clear after the end of the distillation (viscosity~3000 mPa*s, measurement from experiment IL/V180/12-43). After the end of the distillation, the bottoms liquid was diluted to an active content of 88% with 884.45 g of demineralized water within 5 min, and the whole lot was stirred at 48.5° C. to 41.3° C. for about 30 min. The gel from the edge of the flask still had not fully dissolved at this time. After cooling, the system was vented with nitrogen.

The yield was 3761.5 g of clear colourless product.

| The space-time yield was | 6.3 [g (Si)/(l × h)]. |
| Solids content | 45.0% by weight |
| Total alcohol | 0.1% by weight |

The analysis data of the product obtained are compared once again in summary in Table 1.

Comparative Example 4: (Cf. Example 1 from EP1031593A2)

A 4 l four-neck flask with precision glass stirrer, dropping funnel, distillation apparatus, jacketed coil condenser, rotary vane oil pump, bottom thermometer, top thermometer and oil bath with temperature regulation was initially charged with 1250.0 g (69.4 mol) of demineralized water under an $N_2$ blanket. Separately, within 35 minutes, a mixture of 480.0 g (2.17 mol) of Dynasylan® AMEO and 120.0 g (0.46 mol) of AMEO high boilers was added dropwise by means of the metering device (AMEO high boilers is a mixture of Dynasylan® AMEO and about 20% bis-AMEO). In the course of this, the bottom temperature rises from room temperature to 50° C. The mixture was stirred at 50° C. for 3 h. At an absolute pressure of 130 mbar to 100 bar, 450 g of ethanol/water mixture are distilled off at a bottom temperature of 39° C. to 41° C. within about 1.3 h. At the end, the end product is adjusted to a weight of 1500 g with water.

The yield was 1500.0 g of colourless, slightly cloudy product.

| The space-time yield was | 7.2 [g (Si)/(l × h)]. |
| Solids content | 20.1% by weight |
| Total alcohol | not determined |

The analysis data of the product obtained are compared once again in summary in Table 1.

TABLE 1

Comparison of the analysis data of the products obtained from the examples

|  | E 1 | CE 1 | E 2 | CE 2 | E 3 | CE 3 | CE 4 |
|---|---|---|---|---|---|---|---|
| Molar ratio of the feedstocks: water to "silane component" | 12.3:1 | 12.3:1 | 12.3:1 | 6.2:1 | 12.2:1 | 12.3:1 | 26.4:1 |
| Solids content in the product [% by wt.] | 30.7 | 30.8 | 52.8 | 48.6 | 44.7 | 45.0 | 20.1 |
| $SiO_2$ content in the product [% by wt.] | 16.4 | 16.4 | 28.6 | 26.2 | 21.3 | 21.8 | 9.3 |
| Viscosity (20° C.) [mPas] | 10.6 | 11.0 | 550 | 267 | 80.3 | 92 | n.d. |
| Turbidity [FNU] | 0.74 | 0.9 | 1.9 | 0.5 | 0.3 | 1.3 | 4 |
| Total ethanol (after hydrolysis) [% by wt.] | 0.7 | 1.4 | 0.2 | 6.5 | 0.3 | 0.1 | n.d. |
| Free ethanol in the product [% by wt.] | 0.7 | 1.4 | 0.2 | 5.9 | 0.3 | 0.1 | n.d. |
| Colour number [mg Pt—Co/l] | <5 | <5 | <5 | <5 | <5 | <5 | n.d. |
| Space-time yield [g (Si)/(l × h)] | 21.3 | 11.2 | 21.1 | 11.7 | 12.0 | 6.3 | 7.2 |

Comparison of the Results from the Experiments:

Examples E1, CE1, B2 and CE2 (cf. Table 1) were conducted under comparable apparatus conditions. In the case of the procedure according to the invention, the STY and hence the economic viability were much higher compared to U.S. Pat. No. 6,512,132. Moreover, in CE2, a product with a much higher total ethanol content is obtained.

Examples E3 and CE3 can also serve for a comparison of the STYs with regard to the apparatus prerequisites. Thus, Example 3 conducted in accordance with the invention has much better economic viability compared to Comparative Example 3, as demonstrated by the STY. The turbidity value in the product from CE3 is also well above that from E3.

Comparative Example 4 (CE4) corresponds to the teaching according to Example 1 on EP 1031593 A2, except that only a solids content of 20% by weight is achieved therein.

In addition, the metering and/or stirring times in CE1, CE2, CE3 or CE4 are much longer than in the inventive examples E1, E2 and E3.

Furthermore, products according to the invention from E1, E2 and E3 have a high solids content and environmentally advantageous low VOC content (in the form of total ethanol), which constitutes a measure of the completeness of the hydrolysis reaction and hence not least—aside from the exceptional economic viability of the process according to the invention—also a measure of its quality.

The invention claimed is:
1. A process for preparing an aqueous hydrolysate of an aminoalkyltrialkoxysilane, comprising:
   (a) initially charging water, optionally with heating,
   (b) adding one or more hydrolysable silanes comprising at least one aminoalkyltrialkoxysilane in an amount which provides a molar ratio of water to a total amount of aminoalkyltrialkoxysilane of 10.5 to 20:1, and

(c) distilling off an alkyl alcohol formed in the reaction, wherein a solids content in an aqueous composition thus prepared is 30% to 55% by weight, based on the composition, and the aqueous composition has a total content of free and bound alkyl alcohol of not more than 1% by weight, based on the composition.

2. The process of claim 1, wherein the aminoalkyltrialkoxysilane has a formula

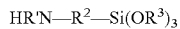

in which
$R^1$ is H or a $C_1$-$C_4$-alkyl group;
$R^2$ is a bivalent $C_1$-$C_4$-alkyl group; and
$R^3$ is a $C_1$-$C_3$-alkyl group.

3. The process of claim 2, wherein $R^1$ is H.

4. The process of claim 2, wherein $R^2$ is a bivalent propyl group [—$(CH_2)_3$-] and $R^3$ is selected from the group consisting of methyl and ethyl.

5. The process of claim 1, wherein the aminoalkyltrialkoxysilane is at least one selected from the group consisting of 3-aminopropyltriethoxysilane and 3-aminopropyltrimethoxysilane.

6. The process of claim 1, wherein the solids content in the aqueous composition thus prepared is 40% to 55% by weight, based on the composition.

7. The process of claim 1, wherein the molar ratio of water to the total amount of aminoalkyltrialkoxysilane is 11 to 18:1.

8. The process of claim 1, wherein a duration of the aminoalkyltrialkoxysilane addition in (b) is 20 to 240 minutes.

9. The process of claim 1, wherein an internal reactor temperature on commencement of the addition of the aminoalkyltrialkoxysilane in (b) is 25° C. to 50° C., and the internal reactor temperature at the end of the addition of the aminoalkyltrialkoxysilane in (b) is 50° C. to 80° C.

10. The process of claim 1, wherein the distilling off of the alkyl alcohol is commenced immediately after the addition of the aminoalkyltrialkoxysilane has ended.

11. The process of claim 1, wherein a period of time between the end of the addition of the aminoalkyltrialkoxysilane and commencement of the distilling off of the alkyl alcohol is less than 5 minutes after attainment of distillation conditions.

12. The process of claim 1, wherein the aqueous composition has a total content of free and bound alkyl alcohol of not more than 0.7% by weight, based on the composition, measured after hydrolysis of a sample of the aqueous composition with sulphuric acid and subsequent neutralization with aqueous sodium carbonate solution by gas chromatography.

13. The process of claim 1, wherein the aqueous composition has a turbidity value of 5 FNU or less measured according to ISO 7027.

* * * * *